US010464912B2

(12) United States Patent
Kalofonos et al.

(10) Patent No.: US 10,464,912 B2
(45) Date of Patent: *Nov. 5, 2019

(54) CHOLINE COCRYSTAL OF EPALRESTAT

(71) Applicant: BIONEVIA PHARMACEUTICALS, INC., Cambridge, MA (US)

(72) Inventors: Isabel Kalofonos, Cambridge, MA (US); G. Patrick Stahly, West Lafayette, IN (US); William Martin-Doyle, Cambridge, MA (US); Dimitris Kalofonos, Cambridge, MA (US); Travis L. Houston, Lafayette, IN (US); Jeffrey S. Stults, West Lafayette, IN (US)

(73) Assignee: BIONEVIA PHARMACEUTICALS, INC., Cambridge, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/449,723

(22) Filed: Mar. 3, 2017

(65) Prior Publication Data

US 2017/0174643 A1 Jun. 22, 2017

Related U.S. Application Data

(60) Continuation of application No. 14/532,517, filed on Nov. 4, 2014, now Pat. No. 9,611,234, which is a division of application No. 13/062,644, filed as application No. PCT/US2009/055868 on Sep. 3, 2009, now Pat. No. 8,906,948.

(60) Provisional application No. 61/094,904, filed on Sep. 6, 2008.

(51) Int. Cl.
| | | |
|---|---|---|
| *A61K 31/427* | (2006.01) | |
| *C07D 277/36* | (2006.01) | |
| *A61K 31/14* | (2006.01) | |
| *A61K 31/426* | (2006.01) | |
| *C07C 215/40* | (2006.01) | |

(52) U.S. Cl.
CPC ............ *C07D 277/36* (2013.01); *A61K 31/14* (2013.01); *A61K 31/426* (2013.01); *A61K 31/427* (2013.01); *C07C 215/40* (2013.01); *C07B 2200/13* (2013.01)

(58) Field of Classification Search
CPC .......................... A61K 31/427; C07D 277/36
See application file for complete search history.

(56) References Cited

U.S. PATENT DOCUMENTS

| | | | |
|---|---|---|---|
| 3,704,245 A | 11/1972 | Umio et al. | |
| 4,443,469 A | 4/1984 | Nishizono | |
| 4,831,045 A | 5/1989 | Tanouchi et al. | |
| 5,145,679 A * | 9/1992 | Hinson ............... | A61K 9/0014 424/401 |
| 6,444,665 B1 | 9/2002 | Helton et al. | |
| 6,696,407 B1 | 2/2004 | Longo et al. | |
| 6,936,601 B2 | 8/2005 | Helton et al. | |
| 7,927,613 B2 | 4/2011 | Almarsson et al. | |
| 2004/0176335 A1 | 9/2004 | Childs | |
| 2005/0181041 A1 | 8/2005 | Goldman | |
| 2011/0275681 A1 | 11/2011 | Kalofonos et al. | |
| 2011/0275695 A1 | 11/2011 | Kalofonos et al. | |

FOREIGN PATENT DOCUMENTS

| | | |
|---|---|---|
| EP | 1106210 A2 | 6/2001 |
| GB | 1247067 | 9/1971 |
| JP | 62-51955 A | 9/1994 |
| JP | 2004-210703 A | 7/2004 |
| JP | 2005-298424 A | 10/2005 |
| JP | 2006-104064 A | 4/2006 |
| JP | 2007-099680 A | 4/2007 |
| WO | 1997/23477 A1 | 7/1997 |
| WO | 00/45818 A1 | 8/2000 |
| WO | 2004/078163 A2 | 9/2004 |
| WO | 2009/152347 A2 | 12/2009 |
| WO | 2010/011922 A2 | 1/2010 |
| WO | 2010/011926 A2 | 1/2010 |
| WO | 2010/028132 A2 | 3/2010 |

OTHER PUBLICATIONS

Berge, et al., "Pharmaceutical Salts", Journal of Pharmaceutical Sciences, vol. 66 (1); pp. 1-19, (1977).
Osol, et al., "Remington's Pharmaceutical Sciences", Philadelphia College of Pharmacy and Science, Sixteenth Edition, pp. 420-425, (1980).
Setoue, et al., "Hyperhomocysteinemia Induced by Guanidinoacetic Acid is Effectively Suppressed by Choline and Betaine in Rats", Biosci. Biotechnol. Biochem., vol. 72 (7), pp. 1696-1703, (2008).
Supplemental European Search Report Application No. EP 09 81 2208.8 dated Apr. 26, 2012.
Baba, et al., "Three-year inhibition of aldose reductase on development of symptomatic neuropathy in diabetic patients",Journal of the Peripheral Nervous System, vol. 11, pp. 176-178, (2006).
Balbach, et al., "Pharmaceutical evaluation of early development candidates—the 100 mg-approach", International Journal of Pharmaceutics, vol. 275, pp. 1-12, (May 4, 2004).
Etter, et al., "Hydrogen bond-directed cocrystallization and molecular recognition properties of diarylureas", J. Am. Chem. Soc., vol. 112 (23), pp. 8415-8426, (1990).

(Continued)

*Primary Examiner* — Sahar Javanmard
(74) *Attorney, Agent, or Firm* — The Marbury Law Group, PLLC

(57) ABSTRACT

The invention relates to a novel choline cocrystal of 5-[(1Z.2E)-2-methyl-3-phenylpropenylidene]-4-oxo-2-thioxo-3-thiazolidineacetic acid. The preparation and characterization of the novel choline cocrystal according to various embodiments of the invention is described. The invention also relates to pharmaceutical compositions containing the novel choline cocrystal and the therapeutic use of the novel choline cocrystal to treat and/or prevent various conditions, including treating and/or preventing diabetic complications, treating and/or preventing homocystinuria reducing levels of homocysteine in blood serum, inhibiting aldose reductase, and affording cardioprotection in non-diabetic patients.

16 Claims, 11 Drawing Sheets

(56) References Cited

OTHER PUBLICATIONS

Goto, et al., "A Placebo-controlled Double-blind Study of Epalrestat (ONO-2235) in Patients with Diabetic Neuropathy", Diabetic Medicine, 10 (Suppl 2); pp. S39-S43, (1993).
Goto, et al., "Effects of an aldose reductase inhibitor, epalrestat, on diabetic neuropathy. Clinical benefit and indication for the drug assessed from the results of a placebo-controlled double-blind study", Biomed & Pharmacother, vol. 49, pp. 269-277, (1995).
Gould, "Salt Selection for basic drugs", International Journal of Pharmaceutics, Mendeley, vol. 33, Issue 1-3, pp. 201-217, (1986).
Hotta, et al., "Clinical Investigation of Epalrestat, an Aldose Reductase Inhibitor, on Diabetic Neuropathy in Japan: Multicenter Study", Journal of Diabetes and its Complications. vol. 10, pp. 168-172, (1996).
Hotta, et al., "Long-Term Clinical Effects of Epalrestat, an Aldose Reductase Inhibitor, on Diabetic Peripheral Neuropathy", Diabetes Care, vol. 29, No. 7, pp. 1538-1544, (Jul. 2006).
Ikeda, et al., "Long-term effect of epalrestat on cardiac autonomic neuropathy in subjects with non-insulin dependent diabetes mellitus", Diabetes Research and Clinical Practice vol. 43, pp. 193-198, (1999).
Ishida, et al., "Conformation of (Z)-3-Carboxymethyl-[2(E)-2-methyl-3-phenylpropenylidene]-rhodanine (Epalrestat), a Potent Aldose Reductase Inhibitor: X-Ray Crystallographic, Energy Calculational, and Nuclear Magnetic Resonance Studies," J. Chem. Soc. Perkin Trans., vol. 2, pp. 1085-1091, (1990).
Ishida, et al., "Structural Elucidation of Epalrestat (ONO-2235), A Potent Aldose Reductase Inhibitor, nd Isomerization of its Double Bonds", Tetrahedron Letters, vol. 30, No. 8, pp. 959-962, (1989).
Kurono, et al., "Photo-Stabilization and Solubilization of an Aldose Reductase Inhibitor, (E)-3-Carboxymethyl-5-[(2E)-methyl-3-phenylpropenylidene]rhodanine (ONO-2235), by Human Serum Albumin", Chem. Pharm. Bull., vol. 35, No. 7, pp. 3045-3048, (1987).

McNamara, et al., "Use of a Glutaric Acid Cocrystal to Improve Oral Bioavailability of Low Solubility API", Pharmaceutical Research, vol. 23, No. 8, pp. 1888-1897, (2006).
Terashima, et al., "Effects of a New Aldose Reductase Inhibitor on Various Tissues in Vitro," The Journal of Pharmacology and Experimental Therapeutics, vol. 229, No. 1, pp. 226-230, (1984).
Wijekoon, et al., "Homocysteine Metabolism in ZDF (Type 2) Diabetic Rats", Diabetes, vol. 54, pp. 3245-3251, (Nov. 2005).
International Search Report for International Publication No. WO 2010/011922 A2 (International Application No. PCT/US2009/051687) dated Mar. 3, 2010.
Written Opinion for International Publication No. WO 2010/011922 A2 (International Application No. PCT/US2009/051687) dated Mar. 3, 2010.
International Search Report for International Publication No. WO 2010/011926 A2 (International Application No. PCT/US2009/051693) dated Mar. 3, 2010.
Written Opinion for International Publication No. WO 2010/011926 A2 (International Application No. PCT/US2009/051693) dated Mar. 3, 2010.
International Search Report for International Publication No. WO 2009/152347 A2 (International Application No. PCT/US2009/047060) dated Jan. 18, 2010.
Written Opinion for International Publication No. WO 2009/152347 A2 (International Application No. PCT/US2009/047060) dated Jan. 18, 2010.
International Search Report for International Publication No. WO 2010/028132 A2 (International Application No. PCT/US2009/055868) dated Apr. 28, 2010.
Written Opinion for International Publication No. WO 2010/028132 A2 (International Application No. PCT/US2009/055868) dated Apr. 28, 2010.
First Examination Report from the Indian Patent Office in corresponding Application No. 2454/DELNP/2011 dated Apr. 28, 2017.

* cited by examiner

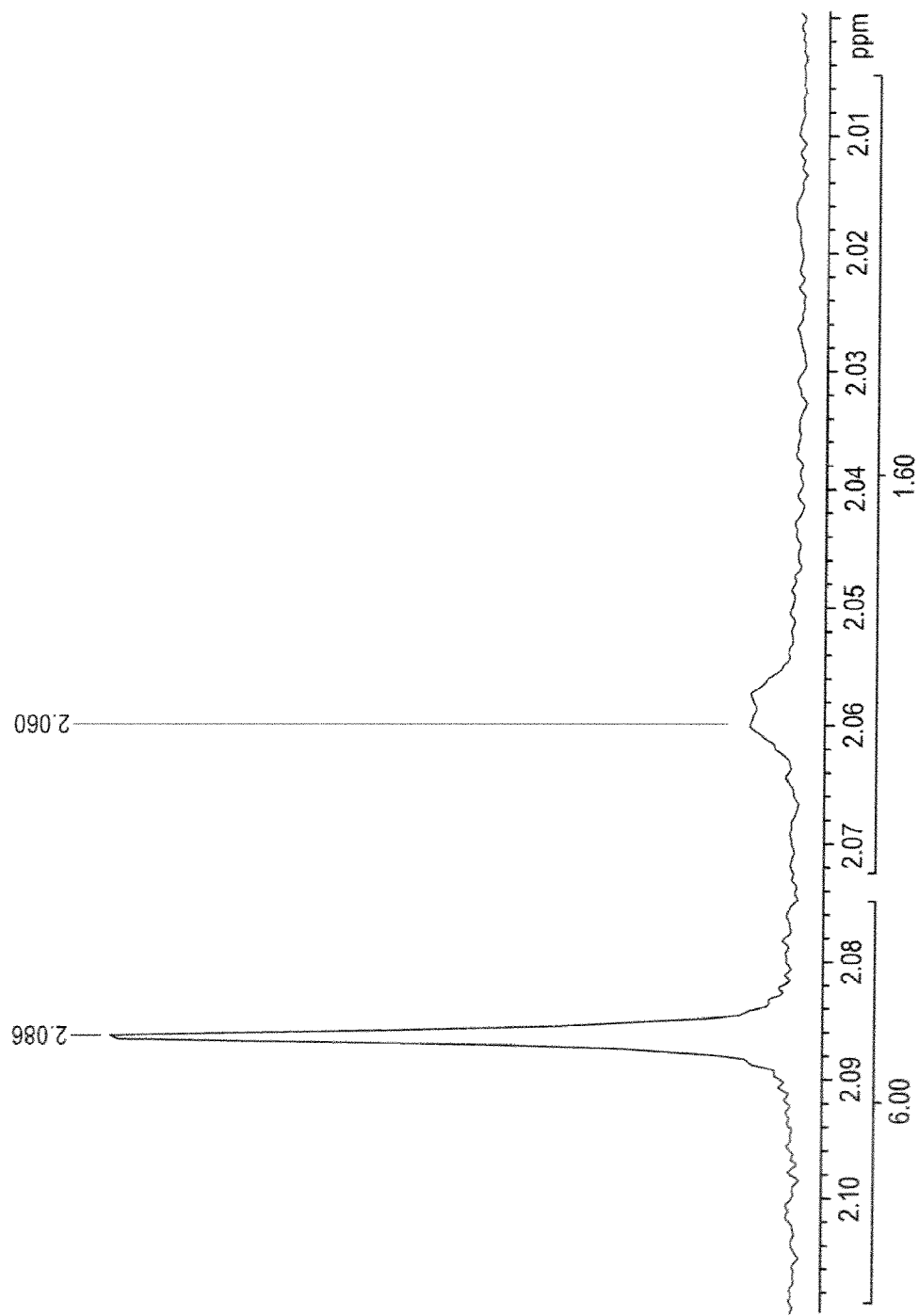

CHOLINE COCRYSTAL OF EPALRESTAT

CROSS-REFERENCE TO RELATED APPLICATIONS

This application is a continuation of application Ser. No. 14/532,517, filed Nov. 4, 2014, which is a divisional of application Ser. No. 13/062,644, filed Jul. 25, 2011, which is a national stage of Application No. PCT/US2009/55868, filed Sep. 3, 2009, and claims priority under 35 U.S.C. § 119 to the benefit of U.S. Provisional Application No. 61/094,904, filed Sep. 6, 2008, all of which are incorporated herein by reference in their entireties.

TECHNICAL FIELD

The invention relates to a novel choline cocrystal of 5-[(1Z,2E)-2-methyl-3-phenylpropenylidene]-4-oxo-2-thioxo-3-thiazolidineacetic acid, processes for making the novel cocrystal, pharmaceutical compositions comprising the novel choline cocrystal, and methods of treating and/or preventing various conditions by administering the novel choline cocrystal.

BACKGROUND

The compound 5-[(1Z,2E)-2-methyl-3-phenylpropenylidene]-4-oxo-2-thioxo-3-thiazolidineacetic acid (shown below), referred to by its common name "epalrestat," is a known active pharmaceutical ingredient ("API") having beneficial therapeutic activity, for example as an aldose reductase inhibitor:

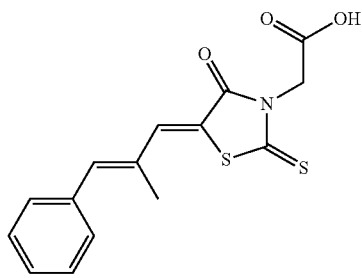 [SMILES: CC(/C=C1\SC(=S)N(CC(=O)O)C1=O)=C\c1ccccc1]

The preparation and pharmacologic activity of epalrestat is described in U.S. Pat. No. 4,831,045. Epalrestat is useful in treating and/or preventing various conditions such as, for example, complications of diabetes, as well as affording cardioprotection in non-diabetic patients. For example, epalrestat has a positive indication for the treatment and/or prevention of diabetic neuropathy, and is useful for the treatment and/or prevention of various other diabetic complications including, for example, diabetic retinopathy, diabetic nephropathy, diabetic cardiomyopathy, diabetic gastroparesis, diabetic microangiopathy, and diabetic microangiopathy in mammals. Epalrestat is also useful in affording cardioprotection to subjects who may not be suffering from diabetes, and as a neuroprotectant or treatment for neurological or neurodegenerative disorders. Therapeutic activity of epalrestat in various conditions has been demonstrated in the clinical literature, including but not limited to Machii H. et al., Gendai Iryo, 1996; 28:1273; Miyamoto S. et al., Gendai Iryo, 1986; 18 (Extra Issue III):82; Goto Y. et al., Journal of Clinical and Experimental Medicine, 1990; 152:405; Nakano K. et al., Journal of Clinical and Experimental Medicine, 1990; 152:137; Okamoto H. et al., Internal Medicine, 2003; 42:655-664; Hamada Y. et al., Diabetes Care 2000; 23:1539-44; Goto Y. et al., Diabet Med 1993; 10(suppl 2):S39-43; Goto Y. et al., Biomed Pharmacother 1995; 49:269-77; Uchida K. et al., Clin Ther 1995; 17:460-6; Hotta N. et al., J Diabetes Complications 1996; 10:168-72; Hotta N. et al., Diabetes Care 2006; 29:1538-44; Matsuoka K. et al., Diabetes Res Clin Pract 2007; 77(suppl 1):S263-8; Nakayama M. et al., Diabetes Care 2001; 24:1093-8; Baba M., Journal of the Peripheral Nervous System 2003; 8:170; Yasuda H. et al., Diabetes Care 2000; 23:705; Ikeda T et al., Diabetes Research and Clinical Practice 1999; 43:193-198; Katayama M. et al., Electrocnccphalography and Clinical Neurophysiology/Electromyography and Motor Control 1995; 97:81; and Misawa S. et al., Neurology 2006; 66:1545-9.

Although therapeutic efficacy is a primary concern for a therapeutic agent, such as epalrestat, the salt and solid state form (e.g. crystalline or amorphous forms) of a drug candidate can be important to its pharmacological properties and to its development as a viable API. For example, each salt or each solid form of a drug candidate can have different solid state (physical and chemical) properties. The differences in physical properties exhibited by a particular solid form of an API, such as a cocrystal, salt, or polymorph of the original compound, can affect pharmaceutical parameters of the API. For example, storage stability, compressibility and density, all of which can be important in formulation and product manufacturing, and solubility and dissolution rates, which may be important factors in determining bioavailability, may be affected. Because these physical properties are often influenced by the solid state form of the API, they can significantly impact a number of factors, including the selection of a compound as an API, the ultimate pharmaceutical dosage form, the optimization of manufacturing processes, and absorption in the body. Moreover, finding the most adequate form for further drug development can reduce the time and the cost of that development.

Obtaining pure crystalline forms, then, is extremely useful in drug development. It may permit better characterization of the drug candidate's chemical and physical properties. For example, crystalline forms often have better chemical and physical properties than amorphous forms. As a further example, a crystalline form may possess more favorable pharmacology than an amorphous form, or may be easier to process. It may also have better storage stability.

One such physical property which can affect processability is the flowability of the solid, before and after milling. Flowability affects the ease with which the material is handled during processing into a pharmaceutical composition. When particles of the powdered compound do not flow past each other easily, a formulation specialist must take that fact into account in developing a tablet or capsule formulation, which may necessitate the use of additional components such as glidants, including, for example, colloidal silicon dioxide, talc, starch, or tribasic calcium phosphate.

Another solid state property of a pharmaceutical compound that may be important is its dissolution rate in aqueous fluid. The rate of dissolution of an active ingredient in a patient's stomach fluid may have therapeutic consequences since it can impact the rate at which an orally administered active ingredient may reach the patient's bloodstream.

Another solid state property of a pharmaceutical compound that may be important is its thermal behavior, including its melting point. The melting point of the solid form of a drug is optionally high enough to avoid melting or plastic deformation during standard processing operations, as well as concretion of the drug by plastic deformation on storage (See. e.g., Gould, P. L. *Int. J. Pharmaceutics* 1986 33 201-217). It may be desirable in some cases for a solid form to melt above about 100° C. For example, melting point categories used by one pharmaceutical company are, in order of preference, +(mp>120° C.), 0 (mp 80-120° C.), and −(mp<80° C.) (Balbach, S.; Korn, C. *Int. J. Pharmaceutics* 2004 275 1-12).

Active drug molecules may be made into pharmaceutically acceptable salts for therapeutic administration to the patient. Crystalline salts of a drug may offer advantages over the free form of the compound, such as improved solubility, stability, processing improvements, etc., and different crystalline salt forms may offer greater or lesser advantages over one another. However, crystalline salt formation is not predictable, and in fact is not always possible. Moreover, there is no way to predict the properties of a particular crystalline salt of a compound until it is formed. As such, finding the right conditions to obtain a particular crystalline salt form of a compound, with pharmaceutically acceptable properties, can take significant time and effort.

It is also possible to achieve desired properties of a particular API by forming a cocrystal of the API itself or of a salt of the API. Cocrystals are crystals that contain two or more non-identical molecules. Examples of cocrystals may be found in the Cambridge Structural Database. Examples of cocrystals may also be found at Etter, M. C., and Adsmond, D. A., J. Chem. Soc., Chem. Commun. 1990 589-591: Etter, M. C., MacDonald, J. C., and Bernstein, J., Acta Crystallogr., Sect. B, Struct. Sci. 1990 B46 256-262; and Etter, M. C., Urbaiczyk-Lipkowska, Z., Zia-Ebrahimi, M., and Panunto, T. W., J. Am. Chem. Soc. 1990 112 8415-8426, which are incorporated herein by reference in their entireties. The following articles are also incorporated herein by reference in their entireties: Görbotz C. H., and Hersleth, H. P. Acta Cryst. 2000 B56 625-534; and Senthil Kumar, V. S., Nangia, A., Katz, A. K., and Carrell, H. L., Crystal Growth & Design. 2002 2 313-318.

By cocrystallizing an API or a salt of an API with a co-former (the other component of the cocrystal), one creates a new solid state form of the API which has unique properties compared with existing solid forms of the API or its salt. For example, a cocrystal may have different dissolution and/or solubility properties than the active agent itself or its salt. Cocrystals containing APIs can be used to deliver APIs therapeutically. New drug formulations comprising cocrystals of APIs with pharmaceutically acceptable co-formers may, in some cases, have superior properties over existing drug formulations. However, cocrystal formation is not predictable, and in fact is not always possible. Moreover, there is no way to predict the properties of a particular cocrystal of a compound until it is formed. As such, finding the right conditions to obtain a particular cocrystal of a compound, with pharmaceutically acceptable properties, can take significant time, effort, and resources.

A crystalline form of a compound, a crystalline salt of the compound, or a cocrystal containing the compound or its salt form generally possesses distinct crystallographic and spectroscopic properties when compared to other crystalline forms having the same chemical composition. Crystallographic and spectroscopic properties of a particular form may be measured by XRPD, single crystal X-ray crystallography, solid state NMR spectroscopy, e.g. $^{13}C$ CP/MAS NMR, or Raman spectrometry, among other techniques. A particular crystalline form of a compound, of its salt, or of a cocrystal, often also exhibits distinct thermal behavior. Thermal behavior can be measured in the laboratory by such techniques as, for example, capillary melting point, TGA, and DSC.

In the following description, various aspects and embodiments of the invention will become evident. In its broadest sense, the invention could be practiced without having one or more features of these aspects and embodiments. Further, these aspects and embodiments are exemplary. Additional objects and advantages of the invention will be set forth in part in the description which follows, and in part will be obvious from the description, or may be learned by practicing the invention. The objects and advantages of the invention will be realized and attained by means of the elements and combinations particularly pointed out in the appended claims.

SUMMARY

In accordance with various embodiments of the invention and after extensive experimentation, the inventors have discovered a novel choline cocrystal of epalrestat, choline hydrogen diepalrestat.

The invention in various embodiments also relates to processes of preparing the novel choline cocrystal of epalrestat, pharmaceutical compositions containing the novel choline cocrystal of epalrestat, and its use in the treatment and/or prevention of various conditions such as diabetic complications, and also to afford cardioprotection in patients who may be non-diabetic.

As used herein, the term "XRPD" refers to x-ray powder diffraction. The XRPD data disclosed herein were obtained using an Inel XRG-3000 diffractometer equipped with a CPS (Curved Position Sensitive) detector with a 2θ range of 120°. Real time data were collected using Cu-Kα radiation at a resolution of 0.03° 2θ. The tube voltage and amperage were set to 40 kV and 30 mA, respectively. The monochromator slit was set at 5 mm by 160 µm. Samples were prepared for analysis by packing them into thin-walled glass capillaries. Each capillary was mounted onto a goniometer head that is motorized to permit spinning of the capillary during data acquisition. Instrument calibration was performed using a silicon reference standard.

As used herein, the term "DSC" refers to differential scanning calorimetry. DSC data disclosed herein were obtained using a TA Instruments differential scanning calorimeter Q2000. The sample was placed into an aluminum DSC pan, and the weight accurately recorded. The pan was crimped and the contents heated under nitrogen under the conditions given in the figures. Indium metal was used as the calibration standard.

As used herein, the term "$^1$H-NMR" refers to proton nuclear magnetic resonance spectroscopy. Solution $^1$H NMR data disclosed herein were acquired on a Varian $UNITY$INOVA-400 spectrometer ($^1$H Larmor Frequency=399.8 MHz). The specific parameters of each spectrum are provided on the attached figures.

As shown below (Example 3), solubility data were collected in water at ambient temperature over approximately 24 hours using an orbital shaker. Samples were taken at approximately 1, 3, 6, and 24 hours, and analyzed by UV spectrophotometry using a SpectraMax M2 UV-VIS spectrophotometer. Wavelength calibration and photometric accuracy were performed using the SpectraMax Pro 5 software as an internal calibration of the instrument. The detector was zeroed with a reference well on a microplate filled with water on which data were obtained, and those data were subtracted from collected data. Samples were analyzed in the UV range at room temperature in the wells of a 96-well quartz plate.

As used herein with respect to the various analytical techniques described herein and data generated therefrom, the term "substantially" the same as or similar to is meant to convey that a particular set of analytical data is, within acceptable scientific limits, sufficiently similar to that disclosed herein such that one of skill in the art would appreciate that the form of the compound is the same as that of the present invention. One of skill in the art would appreciate that certain analytical techniques, such as, for example, XRPD, $^1$H-NMR, and DSC, will not produce exactly the same results every time due to, for example, instrumental variation, sample preparation, scientific error, etc. By way of example only, XRPD results (i.e. peak locations, intensities, and/or presence) may vary slightly from sample to sample, despite the fact that the samples are, within accepted scientific principles, the same form, and this may be due to, for example, preferred orientation or varying solvent or water content. It is well within the ability of those skilled in the art, looking at the data as a whole, to appreciate whether such differences indicate a different form, and thus determine whether analytical data being compared to those disclosed herein are substantially similar. In this regard, and as is commonly practiced within the scientific community, it is not intended that the exemplary analytical data of the novel choline hydrogen diepalrestat disclosed herein be met literally in order to determine whether comparative data represent the same form as that disclosed and claimed herein, such as, for example, whether each and every peak of the exemplary XRPD pattern disclosed herein is present in the comparative data, in the same location, and/or of the same intensity. Rather, as discussed above, it is intended that those of skill in the art, using accepted scientific principles, will make a determination based on the data as a whole regarding whether comparative analytical data represent the same or a different form of the novel choline hydrogen diepalrestat disclosed herein.

As used herein, the terms "choline hydrogen diepalrestat" and "choline hydrogen diacid cocrystal of epalrestat." including variations which use the chemical name "5-[(1Z, 2E)-2-methyl-3-phenylpropenylidene]-4-oxo-2-thioxo-3-thiazolidineacetic acid" in place of the common name "epalrestat," are used interchangeably to refer to the novel choline cocrystal of epalrestat described herein.

It is to be understood that both the foregoing general description and the following detailed description are exemplary and explanatory only and are not restrictive of the invention, as claimed.

BRIEF DESCRIPTION OF THE FIGURES

FIG. 3D is an exemplary $^1$H-NMR spectrum from 2.11 to 2.00 ppm of a choline hydrogen diacid cocrystal of epalrestat, according to one embodiment of the invention;

DESCRIPTION OF EXEMPLARY EMBODIMENTS

The invention relates to a novel choline cocrystal of epalrestat. Specifically, the novel cocrystal which has been discovered is a choline hydrogen diacid cocrystal of epalrestat having two moles of epalrestat and one mole of choline. In one embodiment, the novel cocrystal is anhydrous. At least one exemplary method of preparation of the novel choline cocrystal of epalrestat according to the invention is described below in the examples.

Figure 1:
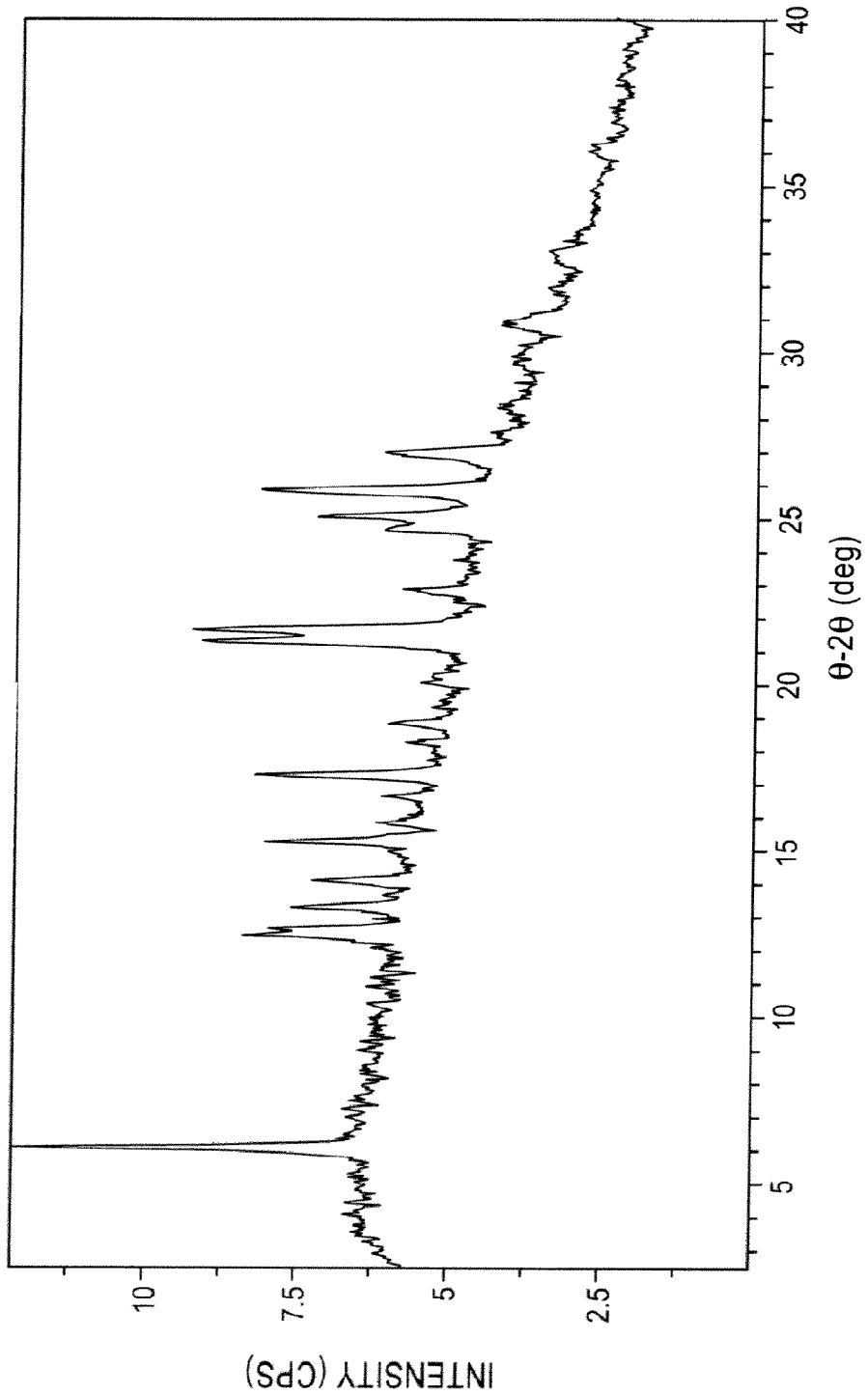
FIG. 1 is an exemplary XRPD pattern of a choline hydrogen diacid cocrystal of epalrestat, according to one embodiment of the invention.

The novel cocrystal described herein is obtained in a crystalline solid form, as seen by the high degree of crystallinity depicted in the XRPD pattern provided in FIG. 1. The cocrystal is shown to have distinct physicochemical properties. The cocrystal of epalrestat described herein is particularly suitable for the preparation of stable pharmaceutical preparations.

Figure 2:
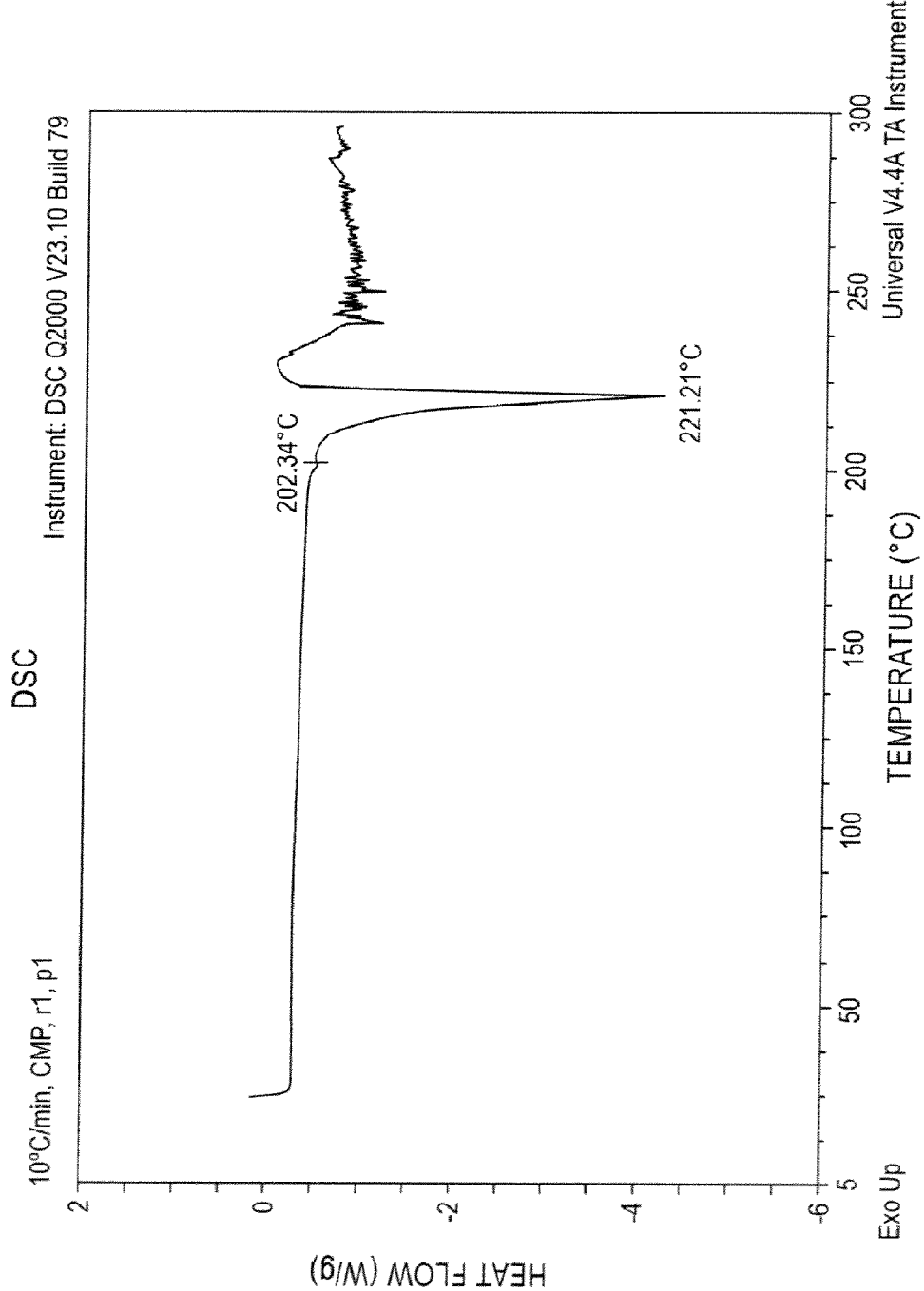
FIG. 2 is an exemplary DSC thermogram of a choline hydrogen diacid cocrystal of epalrestat, according to one embodiment of the invention.
Figure 3A:
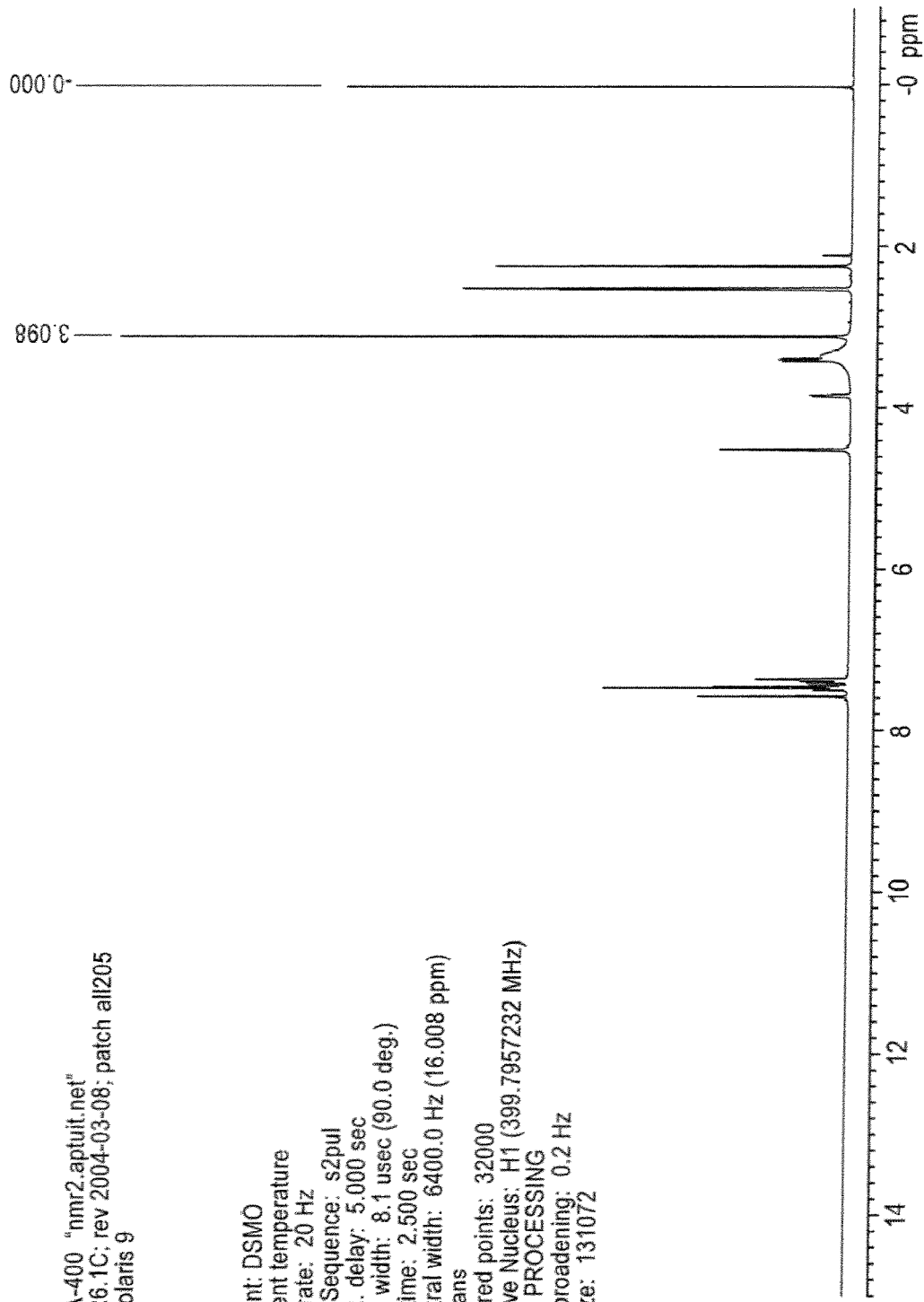
FIG. 3A is an exemplary full $^1$H-NMR spectrum of a choline hydrogen diacid cocrystal of epalrestat, according to one embodiment of the invention.
Figure 3B:
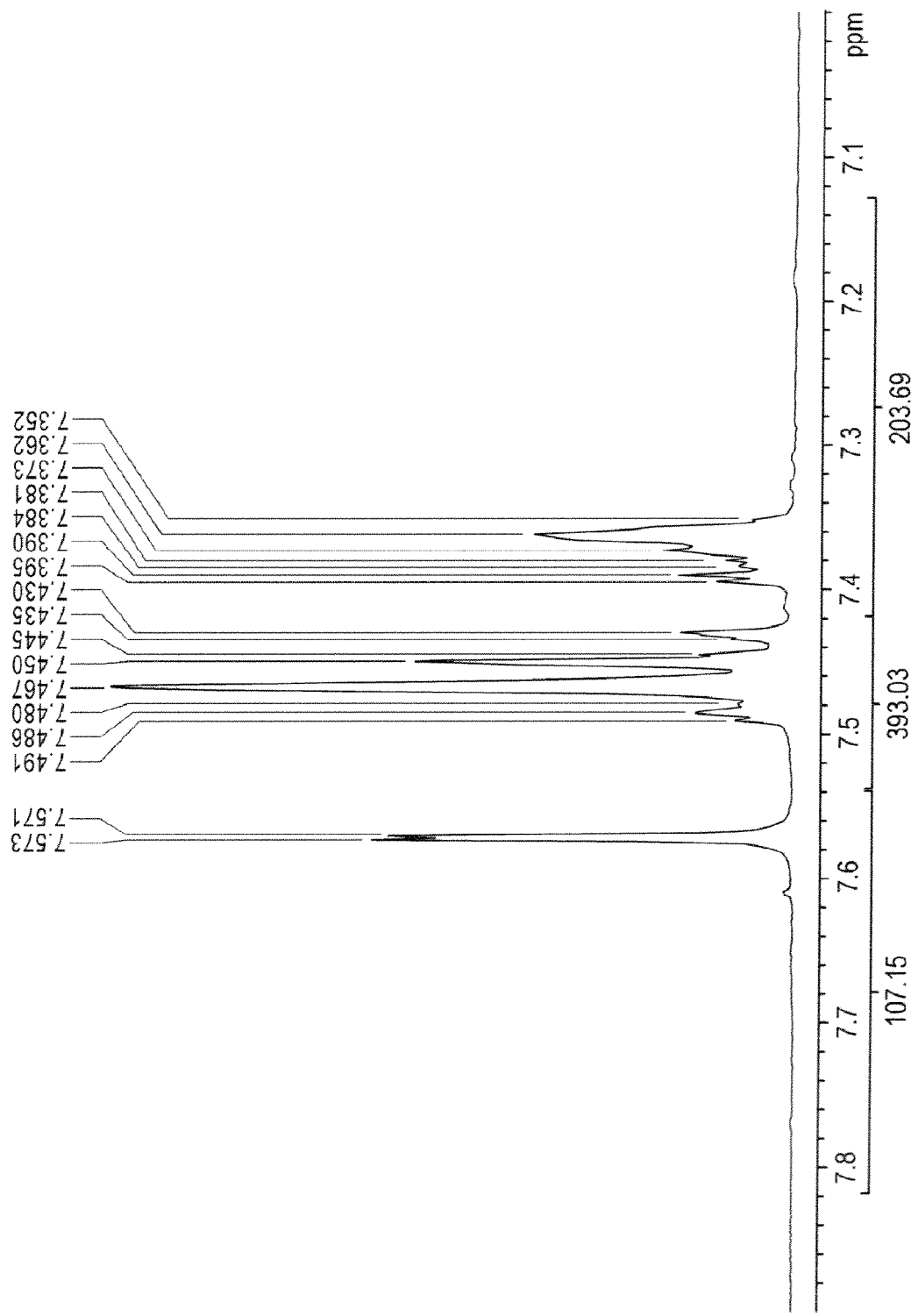
FIG. 3B is an exemplary $^1$H-NMR spectrum from 7.9 to 7.0 ppm of a choline hydrogen diacid cocrystal of epalrestat, according to one embodiment of the invention.
Figure 3C:
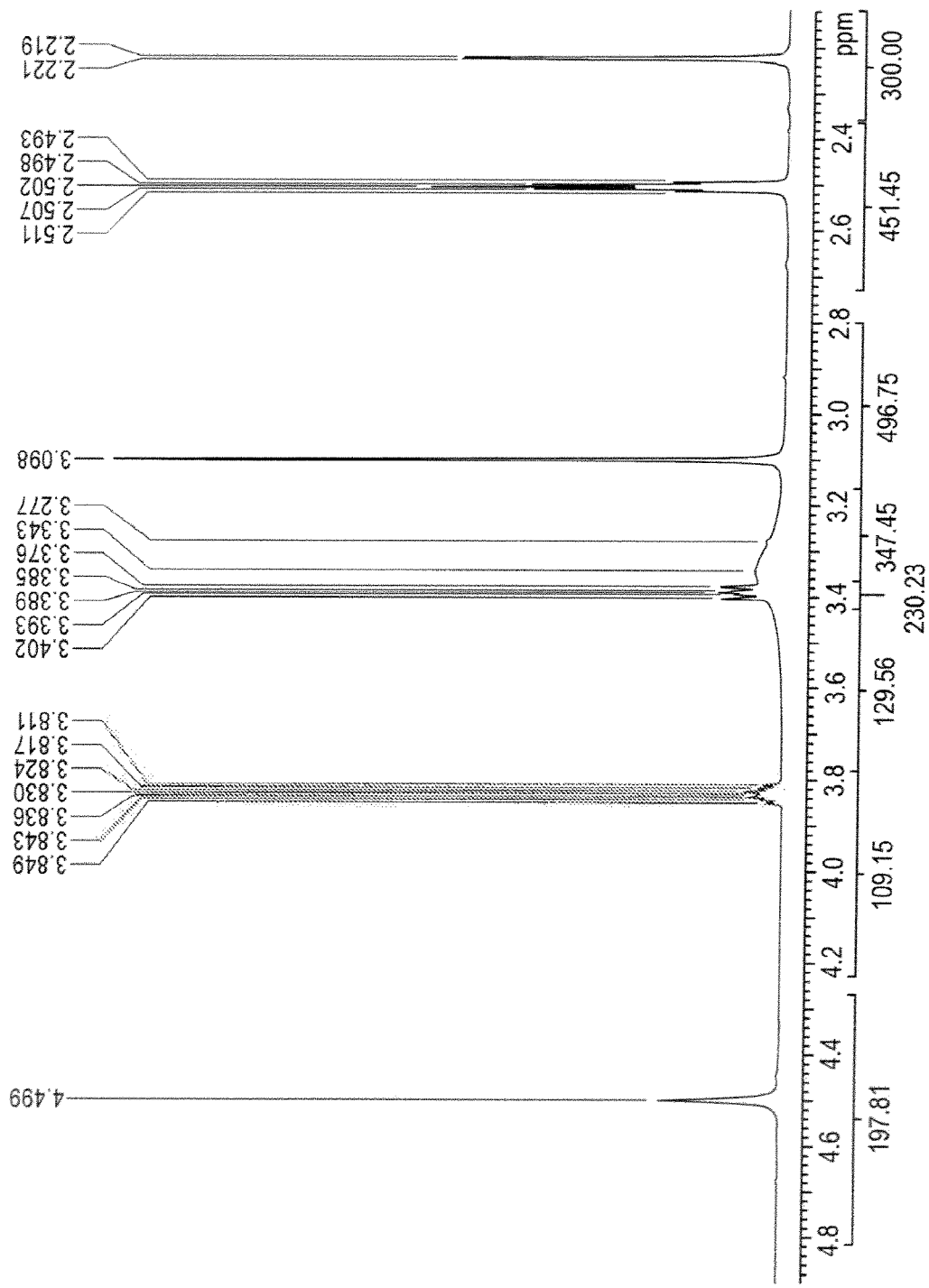
FIG. 3C is an exemplary $^1$H-NMR spectrum from 4.8 to 2.2 ppm of a choline hydrogen diacid cocrystal of epalrestat, according to one embodiment of the invention.
Figure 6A:
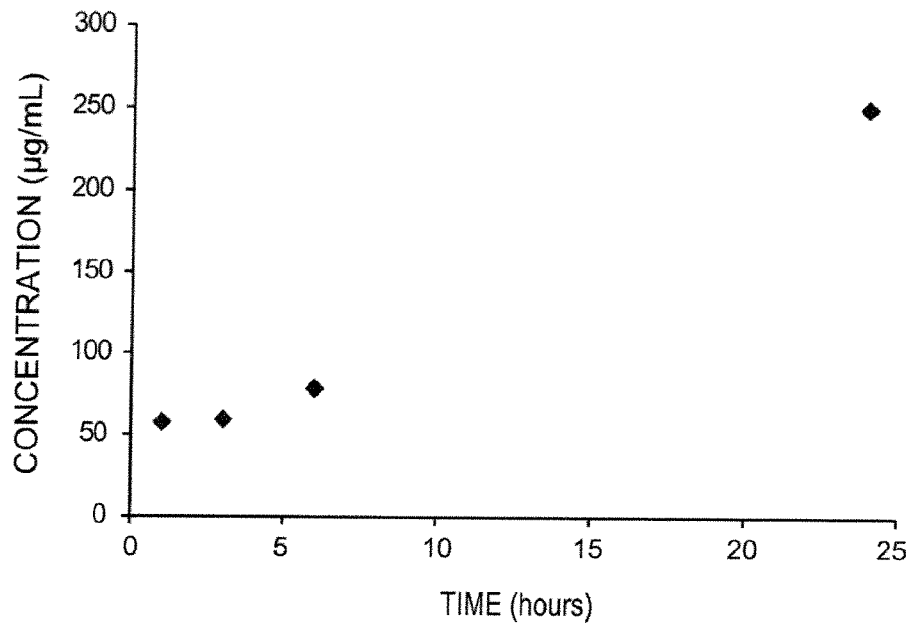
FIGS. 6A-6B show solubility data for a choline cocrystal of epalrestat, according to one exemplary embodiment of the invention.

The novel choline cocrystal of epalrestat is characterized by an XRPD pattern substantially as shown in FIG. 1, a DSC thermogram substantially as shown in FIG. 2, an $^1$H-NMR spectrum substantially as shown in FIGS. 3A-3D, and a solubility profile substantially as shown in FIG. 6A. An exemplary listing of representative XRPD peaks of the novel choline cocrystal of epalrestat according to an embodiment of the invention can be found in Table 1. An exemplary listing of representative NMR data can be found in Table 2.

TABLE 1

| °2θ | d space (Å) | Intensity (%) |
|---|---|---|
| 6.1 ± 0.2 | 14.51 ± 0.48 | 100 |
| 12.4 ± 0.2 | 7.11 ± 0.11 | 47 |
| 12.7 ± 0.2 | 6.99 ± 0.11 | 41 |
| 13.3 ± 0.2 | 6.66 ± 0.10 | 35 |
| 14.1 ± 0.2 | 6.28 ± 0.09 | 31 |
| 15.3 ± 0.2 | 5.80 ± 0.08 | 46 |
| 15.8 ± 0.2 | 5.60 ± 0.07 | 16 |
| 16.6 ± 0.2 | 5.33 ± 0.06 | 17 |
| 17.2 ± 0.2 | 5.14 ± 0.06 | 50 |
| 18.2 ± 0.2 | 4.86 ± 0.05 | 13 |

TABLE 1-continued

| °2θ | d space (Å) | Intensity (%) |
|---|---|---|
| 18.8 ± 0.2 | 4.72 ± 0.05 | 19 |
| 20.0 ± 0.2 | 4.43 ± 0.04 | 13 |
| 20.2 ± 0.2 | 4.39 ± 0.04 | 9 |
| 21.3 ± 0.2 | 4.18 ± 0.04 | 72 |
| 21.6 ± 0.2 | 4.11 ± 0.04 | 78 |
| 22.9 ± 0.2 | 3.89 ± 0.03 | 23 |
| 24.6 ± 0.2 | 3.62 ± 0.03 | 31 |
| 25.0 ± 0.2 | 3.56 ± 0.03 | 50 |
| 25.8 ± 0.2 | 3.45 ± 0.03 | 67 |
| 27.0 ± 0.2 | 3.31 ± 0.02 | 37 |
| 28.4 ± 0.2 | 3.15 ± 0.02 | 9 |

TABLE 2

| protons | peak position (ppm) | multiplicity | coupling constant (Hz) | number of protons |
|---|---|---|---|---|
| impurity | 2.06 | multiplet | — | low intensity |
| impurity | 2.09 | singlet | — | low intensity |
| $CH_3$ | 2.22 | doublet | 0.9 | 3 |
| $CH_3$ (choline) | 3.10 | singlet | — | 4.5, partially obscured by water |
| $CH_2$ (choline) | 3.38-3.40 | multiplet | — | obscured by water |
| $CH_2$ (choline) | 3.81-3.85 | multiplet | — | 1 |
| $CH_2$ | 4.50 | singlet | — | 2 |
| olefin/aromatic | 7.35-7.40 | multiplet | — | 2 |
| olefin/aromatic | 7.43-7.49 | multiplet | — | 4 |
| olefin | 7.57 | doublet | 0.8 | 1 |

Pharmaceutical Compositions and Methods of Treatment and/or Prevention

The novel choline cocrystal of epalrestat described herein possesses the same general pharmacological activity as epalrestat free acid, and is useful for treating and/or preventing diabetic complications such as those discussed above, including, for example, diabetic neuropathy, diabetic retinopathy, and diabetic nephropathy. By use of the term "treating" or "alleviating" it is meant decreasing the symptoms, markers, or any negative effects of a condition in any appreciable degree in a patient who currently has the condition, and by "preventing" it is meant preventing entirely or preventing to some extent, such as, for example, by delaying the onset or lessening the degree to which a patient develops the condition.

Accordingly, various embodiments of the invention include methods for preventing and/or treating cardiac tissue ischemia in a mammal comprising administering to said mammal an effective amount of a novel choline cocrystal of epalrestat as described herein. Various embodiments of the invention also include methods for treating and/or preventing cardiac tissue ischemia in a mammal comprising administering to said mammal a pharmaceutical composition comprising a novel choline cocrystal of epalrestat and a pharmaceutically acceptable vehicle, carrier, and/or diluent. In exemplary methods, said mammal may be suffering from cardiac tissue ischemia or may be at risk of suffering from cardiac tissue ischemia. For example, a mammal at risk may be awaiting or undergoing cardiac, cardiovascular, or other major surgery. Thus, various embodiments of the invention include methods for providing myocardial protection during surgery or myocardial protection in patients presenting with ongoing cardiac or cerebral ischemic events or chronic cardioprotection in patients diagnosed with, or at risk for, coronary heart disease, cardiac dysfunction or myocardial stunning. As used herein, "mammal" is intended to include humans.

Various embodiments of the invention include methods of inhibiting aldose reductase in a mammal in need of inhibition of aldose reductase comprising administering an aldose reductase inhibiting amount of a novel choline cocrystal of epalrestat as described herein. Various embodiments of the invention also include methods of inhibiting aldose reductase in a mammal in need of inhibition of aldose reductase comprising administering a pharmaceutical composition comprising a novel choline cocrystal of epalrestat as described herein, and a pharmaceutically acceptable vehicle, carrier, and/or diluent.

Additional embodiments of the invention include methods of treating and/or preventing one or more diabetic complications in a mammal suffering from one or more diabetic complications comprising administering to said mammal an effective amount of a novel choline cocrystal of epalrestat as described herein. Diabetic complications which may be treated and/or prevented by exemplary methods of the invention include, but are not limited to, diabetic neuropathy, diabetic nephropathy, diabetic cardiomyopathy, diabetic retinopathy, diabetic gastroparesis, cataracts, foot ulcers, diabetic macroangiopathy, and diabetic microangiopathy. Various embodiments of the invention are also directed to methods of treating and/or preventing one or more diabetic complications in a mammal suffering from one or more diabetic complications comprising administering to said mammal an effective amount of a pharmaceutical composition as set forth herein.

Further embodiments of the invention contemplate methods of treating and/or preventing homocystinuria, and/or reducing levels of homocysteine in the blood serum, for example in a patient with diabetes, by administering an effective amount of a novel choline cocrystal of epalrestat, or composition and/or formulation comprising an effective amount of a novel choline cocrystal of epalrestat, as described herein. In vivo, choline is converted to betaine, also known as trimethylglycine or glycine betaine. Both choline and betaine are naturally occurring molecules found in dietary sources (Olthof M R, Curr Drug Metab 2005; 6:15-22). In biological systems, betaine is important in the metabolism of homocysteine, and functions as a methyl donor. Betaine is therefore used therapeutically to reduce elevated homocysteine concentrations (van Guldener C et al, Expert Opinion on Pharmacotherapy 2001; 2:1449-1460), and is approved for use in the U.S. and Europe as a therapeutic agent to treat homocystinuria from genetic causes (Cystadane prescribing information, FDA; Cystadane product information, EMEA). In animal studies, dietary choline deprivation has also been shown to lead to elevated homocysteinc (Setoue M et al, J Nutr Sci Vitaminol 2008; 54:483-90), and choline supplementation has been shown to reduce elevated homocysteine levels (Setoue M et al, Biosci Biotechnol Biochem 2008; 72:1696-703). In humans, epidemiologic studies have shown the general population to have dietary choline intake levels below the recommended adequate intake level (Bidulescu A et al, Nutr J 2009; 8:14), and in pilot studies, choline supplementation has lowered elevated homocysteine levels (Olthof M R et al, Am J Clin Nutr 2005; 82:111-7). Elevated homocysteine is associated with cardiovascular disease in both Type 2 diabetes (Hoogeveen E K et al, Arterioscler Thromb Vasc Biol 1998; 18:133-138) and in non-diabetic populations (Bostom A G et al, Arch Intern Med 1999; 159:1077-1080). Homocysteine is also elevated in patients with various non-cardiovascular diabetic complications, including diabetic nephropathy (Bostom A G et al, Arterioscler Thromb Vasc Biol 1997; 17:2554-2558), diabetic retinopathy (Brazionis L et al, Diabetes Care 2008; 31:50-56), and diabetic neuropathy (Ambrosch A et al, Diabetic Medicine 2001; 18:185-192). Administration of a novel choline cocrystal of epalrestat may therefore have an additional beneficial therapeutic effect for treating these conditions.

Various additional embodiments of the invention include methods of palliating neurological disorders and delaying development of neurological disorders using aldose reductase inhibitors, in order to modulate neurotrophic factor-associated activity, especially CNTF-associated levels and activity, for example as disclosed in U.S. Pat. No. 6,696,407. These methods are useful, for example, for a condition or circumstance in which neurotrophic factor-associated activity is indicated, such as neurological disorders, including neurodegenerative disorders. A "neurological disorder" as used herein means an aberration from clinically normal neural cell activity (i.e., compromised neural cell activity) and includes, by way of example only, neurodegenerative disease (of the CNS and/or PNS), neuropathies associated with toxicity (neurotoxicity) such as chemotherapy (i.e., vincristine or cisplatin-induced motor neuropathy) and alcohol consumption, immune-mediated neurodiseases such as multiple sclerosis (MS) and Guillain-Barre syndrome, hereditary neuropathies such as Charcot-Marie-Tooth neuropathies [see Lebo et al. (1992) Am. J. Hum. Genet. 50:42-55], injury due to trauma, and compromised function due to senescence. Examples of neurodegenerative disorders include but are not limited to, Huntington's disease, amyotrophic lateral sclerosis (ALS), Alzheimer's disease, Parkinson's disease, and Shy-Drager syndrome. The methods may also be useful in delaying development of a neurological disorder, and thus may be used in individuals who show no overt signs of disease but are, for example, at risk of developing disease.

As discussed, additional embodiments of the invention relate to pharmaceutical compositions comprising any amount, such as a therapeutically effective amount, of a novel choline cocrystal of epalrestat as described herein and a pharmaceutically acceptable carrier or excipient. The novel choline cocrystal of epalrestat according to the invention has the same or similar pharmaceutical activity as previously reported for epalrestat free acid. Pharmaceutical compositions for the treatment and/or prevention of those conditions or disorders may contain some amount, for example a therapeutically effective amount, of a novel choline cocrystal of epalrestat described herein, as appropriate. e.g. for treatment of a patient with the particular condition or disorder. As a further example, the amount of the cocrystal in the pharmaceutical compositions may likewise be lower than a therapeutically effective amount, and may, for example, be in the composition in conjunction with another compound or form of epalrestat which, when combined, are present in a therapeutically effective amount. A "therapeutically effective amount" as described herein refers to an amount of a therapeutic agent sufficient to treat, alleviate, and/or prevent a condition treatable and/or preventable by administration of a composition of the invention, in any degree. That amount can be an amount sufficient to exhibit a detectable therapeutic or preventative or ameliorative effect, and can be determined by routine experimentation by those of skill in the art. The effect may include, for example, treatment, alleviation, and/or prevention of the conditions listed herein. The actual amount required, e.g. for treatment of any particular patient, will depend upon a variety of factors including the disorder being treated and/or prevented; its severity; the specific pharmaceutical composition employed; the age, body weight, general health, gender, and diet of the patient; the mode of administration; the time of administration; the route of administration; the rate of excretion of epalrestat; the duration of the treatment; any drugs used in combination or coincidental with the specific compound employed; and other such factors well known in the medical arts. These factors are discussed in Goodman and Gilman's "The Pharmacological Basis of Therapeutics", Tenth Edition, A. Gilman, J. Hardman and L. Limbird, eds., McGraw-Hill Press, 155-173, 2001.

A pharmaceutical composition according to various embodiments of the invention may be any pharmaceutical form which contains a novel choline cocrystal of epalrestat as described herein. Depending on the type of pharmaceutical composition, the pharmaceutically acceptable carrier may be chosen from any one or a combination of carriers known in the art. The choice of the pharmaceutically acceptable carrier depends upon the pharmaceutical form and the desired method of administration to be used. For a pharmaceutical composition according to various embodiments of the invention, that is one having a novel choline cocrystal of epalrestat as described herein, a carrier may be chosen that maintains the cocrystal form. In other words, the carrier, in some embodiments, will not substantially alter the cocrystal form of epalrestat as described herein. In some embodiments, the carrier will similarly not be otherwise incompatible with epalrestat itself, such as by producing any undesirable biological effect or otherwise interacting in a deleterious manner with any other component(s) of the pharmaceutical composition.

The pharmaceutical compositions according to various embodiments of the invention are optionally formulated in unit dosage form for ease of administration and uniformity of dosage. A "unit dosage form" refers to a physically discrete unit of therapeutic agent appropriate for the patient to be treated. It will be understood, however, that the total daily dosage of a novel choline cocrystal of epalrestat described herein and pharmaceutical compositions thereof will be decided by the attending physician within the scope of sound medical judgment using known methods.

Because the novel choline cocrystal of epalrestat as described herein is more easily maintained during preparation, solid dosage forms are a preferred form for the pharmaceutical composition of the invention. Solid dosage forms for oral administration may include, for example, capsules, tablets, pills, powders, and granules. In one exemplary embodiment, the solid dosage form is a tablet. The active ingredient may be contained in a solid dosage form formulation that provides quick release, sustained release, or delayed release after administration to the patient. In such solid dosage forms, the active compound may be mixed with at least one inert, pharmaceutically acceptable carrier, such as, for example, sodium citrate or dicalcium phosphate. The solid dosage form may also include one or more of various additional ingredients, including, for example: a) fillers or extenders such as, for example, starches, lactose, sucrose, glucose, mannitol, and silicic acid; b) binders such as, for example, carboxymethylcellulose, alginates, gelatin, polyvinylpyrrolidinone, sucrose, and acacia; c) humectants such as, for example, glycerol; d) disintegrating agents such as, for example, agar, calcium carbonate, potato or tapioca starch, alginic acid, certain silicates, and sodium carbonate; e) dissolution retarding agents such as, for example, paraffin; f) absorption accelerators such as, for example, quaternary ammonium compounds; g) wetting agents such as, for example, cetyl alcohol and glycerol monostearate; h) absorbents such as, for example, kaolin and bentonite clay; and i) lubricants such as, for example, talc, calcium stearate, magnesium stearate, solid polyethylene glycols, and sodium lauryl sulfate. The solid dosage forms may also comprise buffering agents. They may optionally contain opacifying agents and can also be of a composition that they release the active ingredient(s) only, or preferentially, in a certain part of the intestinal tract, optionally, in a delayed manner. Remington's Pharmaceutical Sciences, Sixteenth Edition, E. W. Martin (Mack Publishing Co., Easton, Pa., 1980) discloses various carriers used in formulating pharmaceutical compositions and known techniques for the preparation thereof. Solid dosage forms of pharmaceutical compositions according to various embodiments of the invention can also be prepared with coatings and shells such as enteric coatings and other coatings well known in the pharmaceutical formulating art.

The novel choline cocrystal of epalrestat described herein can be, in one exemplary embodiment, administered in a solid micro-encapsulated form with one or more carriers as discussed above. Microencapsulated forms may also be used in soft and hard-filled gelatin capsules with carriers such as lactose or milk sugar as well as high molecular weight polyethylene glycols and the like.

The novel choline cocrystal of epalrestat as described herein may also be used in the preparation of non-solid formulations, e.g., injectables and patches, of epalrestat. Such non-solid formulations are known in the art. In a non-solid formulation, the cocrystal form may, in certain exemplary embodiments, not be maintained. For example, the cocrystal may be dissolved in a liquid carrier. In this case, the novel cocrystal of epalrestat described herein may represent intermediate forms of epalrestat used in the preparation of the non-solid formulation. The novel choline cocrystal of epalrestat described herein may provide advantages of handling stability and purity to the process of making such formulations.

The invention also relates to the treatment and/or prevention of diabetes-associated disorders such as those discussed above. The invention provides a method for treating and/or preventing diabetes-associated disorders by administering to mammals a novel choline cocrystal of epalrestat as described herein, or a pharmaceutical composition containing the same, in an amount sufficient to treat and/or prevent a condition treatable and/or preventable by administration of a composition of the invention. That amount is the amount sufficient to exhibit any detectable therapeutic and/or preventative or ameliorative effect. The effect may include, for example, treatment and/or prevention of the conditions listed herein. The novel choline cocrystal of epalrestat and pharmaceutical compositions containing the same may, according to various embodiments of the invention, be administered using any amount, any form of pharmaceutical composition, and any route of administration effective, e.g. for treatment, all of which are easily determined by those of skill in the art through routine experimentation. After formulation with an appropriate pharmaceutically acceptable carrier in a desired dosage, as known by those of skill in the art, the pharmaceutical compositions can be administered to humans and other mammals by any known method, such as, for example, orally, rectally, or topically (such as by powders or other solid form-based topical formulations). In certain embodiments, the novel choline cocrystal of epalrestat according to the invention may be administered at dosage levels ranging from about 0.001 mg/kg to about 50 mg/kg, from about 0.01 mg/kg to about 25 mg/kg, or from about 0.1 mg/kg to about 10 mg/kg of subject body weight per day, one or more times a day, to obtain the desired therapeutic effect. It will also be appreciated that dosages smaller than about 0.001 mg/kg or greater than about 50 mg/kg (for example, ranging from about 50 mg/kg to about 100 mg/kg) can also be administered to a subject in certain embodiments of the invention. As discussed above, the amount required for a particular patient will depend upon a variety of factors including the disorder being treated and/or prevented; its severity; the specific pharmaceutical composition employed; the age, body weight, general health, gender, and diet of the patient; the mode of administration; the time of administration; the route of administration; the rate of excretion of epalrestat; the duration of the treatment; any drugs used in combination or coincidental with the specific compound employed; and other such factors well known in the medical arts. And, as also discussed, the pharmaceutical compositions comprising a novel choline cocrystal of epalrestat as described herein may be administered as a unit dosage form.

Although the present invention herein has been described with reference to various exemplary embodiments, it is to be understood that these embodiments are merely illustrative of the principles and applications of the present invention. Those having skill in the art would recognize that a variety of modifications to the exemplary embodiments may be made, without departing from the scope of the invention.

Moreover, it should be understood that various features and/or characteristics of differing embodiments herein may be combined with one another. It is therefore to be understood that numerous modifications may be made to the illustrative embodiments and that other arrangements may be devised without departing from the scope of the invention.

Furthermore, other embodiments of the invention will be apparent to those skilled in the art from consideration of the specification and practice of the invention disclosed herein. It is intended that the specification and examples be considered as exemplary only, with a scope and spirit being indicated by the claims.

EXAMPLES

Example 1—Preparation of the Intermediate Product

Figure 4:
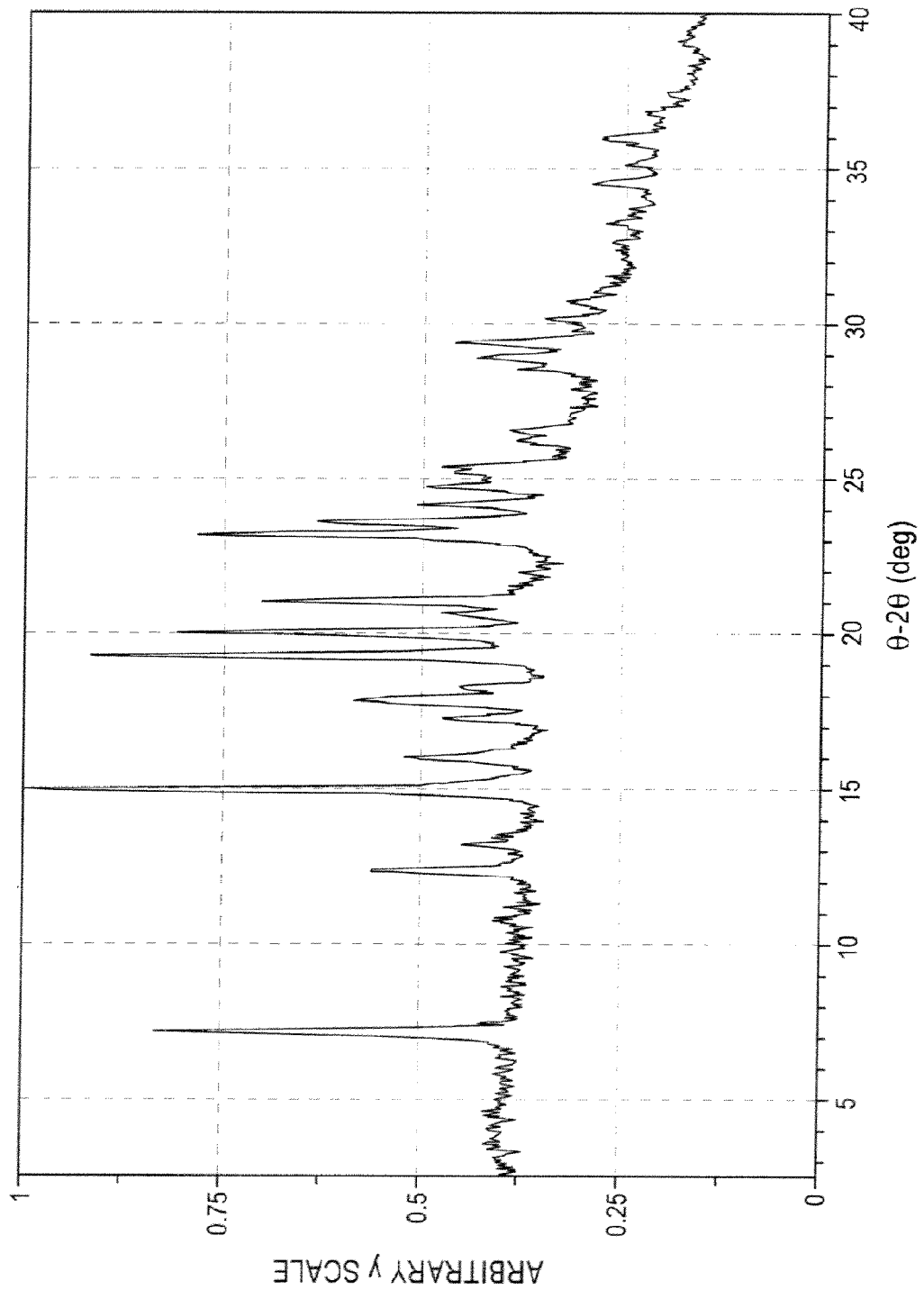
FIG. 4 is an XRPD pattern of an intermediate product useful in an exemplary method of making a choline hydrogen diacid cocrystal of epalrestat according to one embodiment of the invention.
Figure 5A:
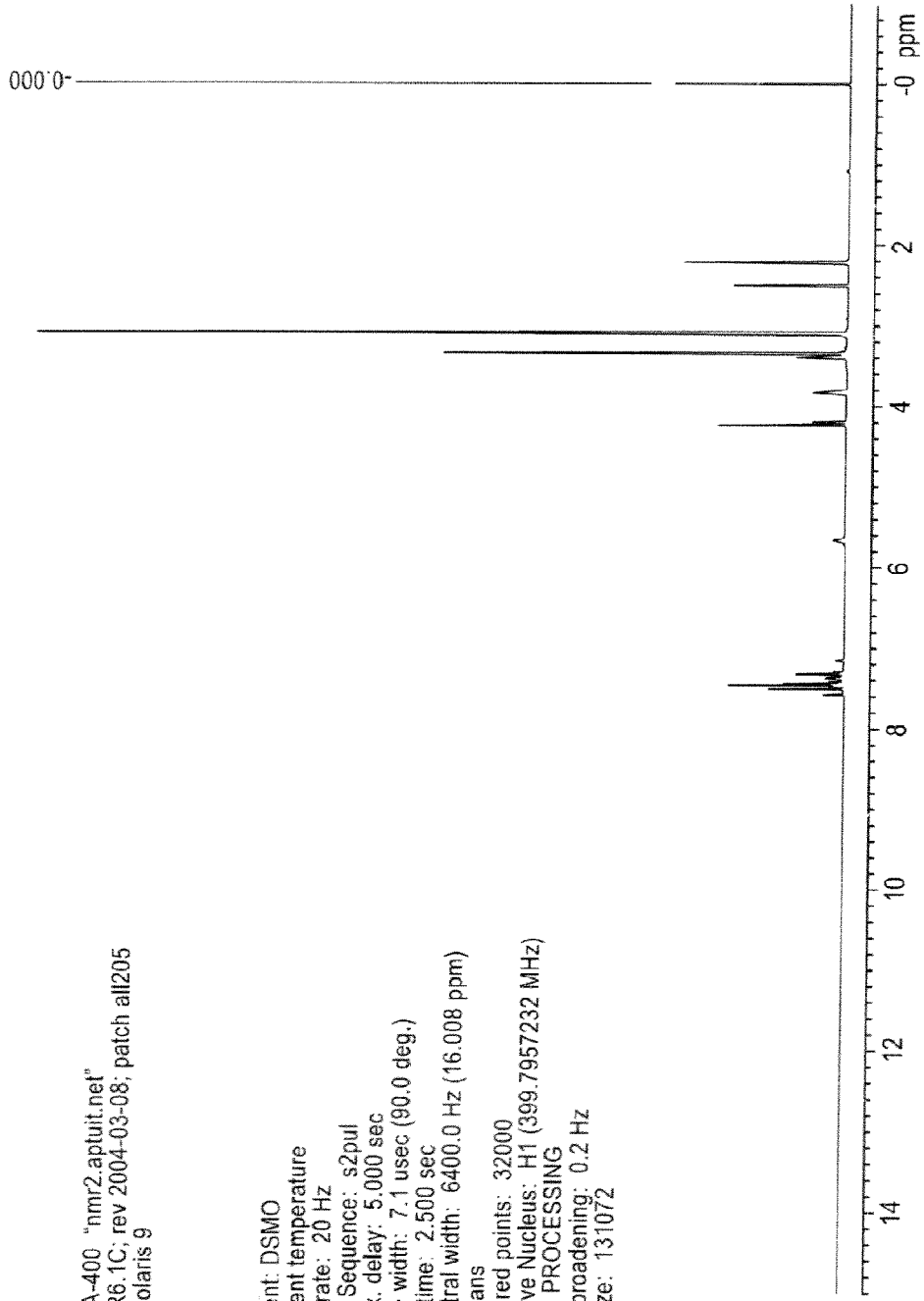
FIG. 5A is a full $^1$H-NMR spectrum of an intermediate product useful in an exemplary method of making a choline hydrogen diacid cocrystal of epalrestat according to one embodiment of the invention.
Figure 5B:
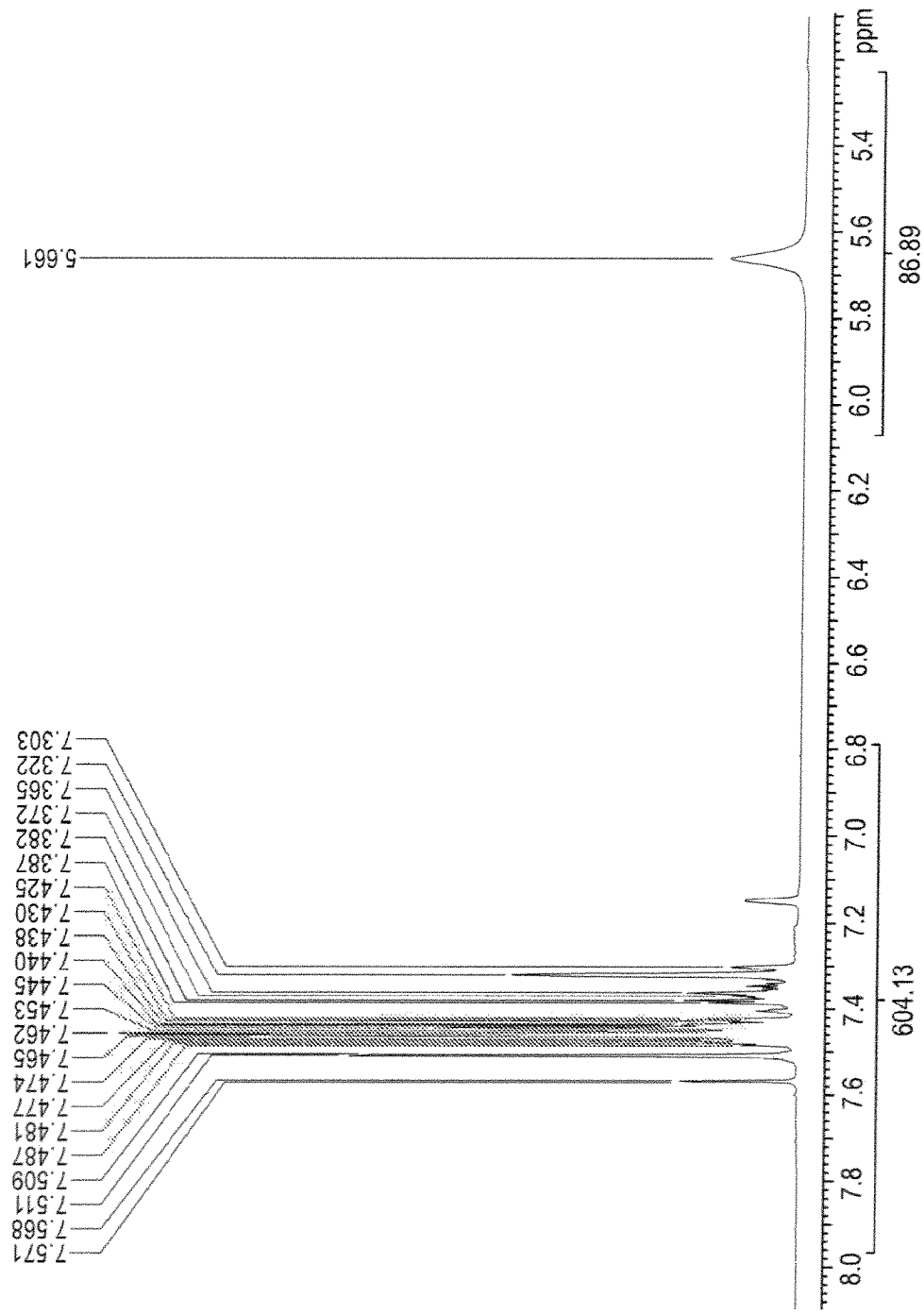
FIG. 5B is an $^1$H-NMR spectrum from 8.0 to 5.4 ppm of an intermediate product useful in an exemplary method of making a choline hydrogen diacid cocrystal of epalrestat according to one embodiment of the invention.
Figure 5C:
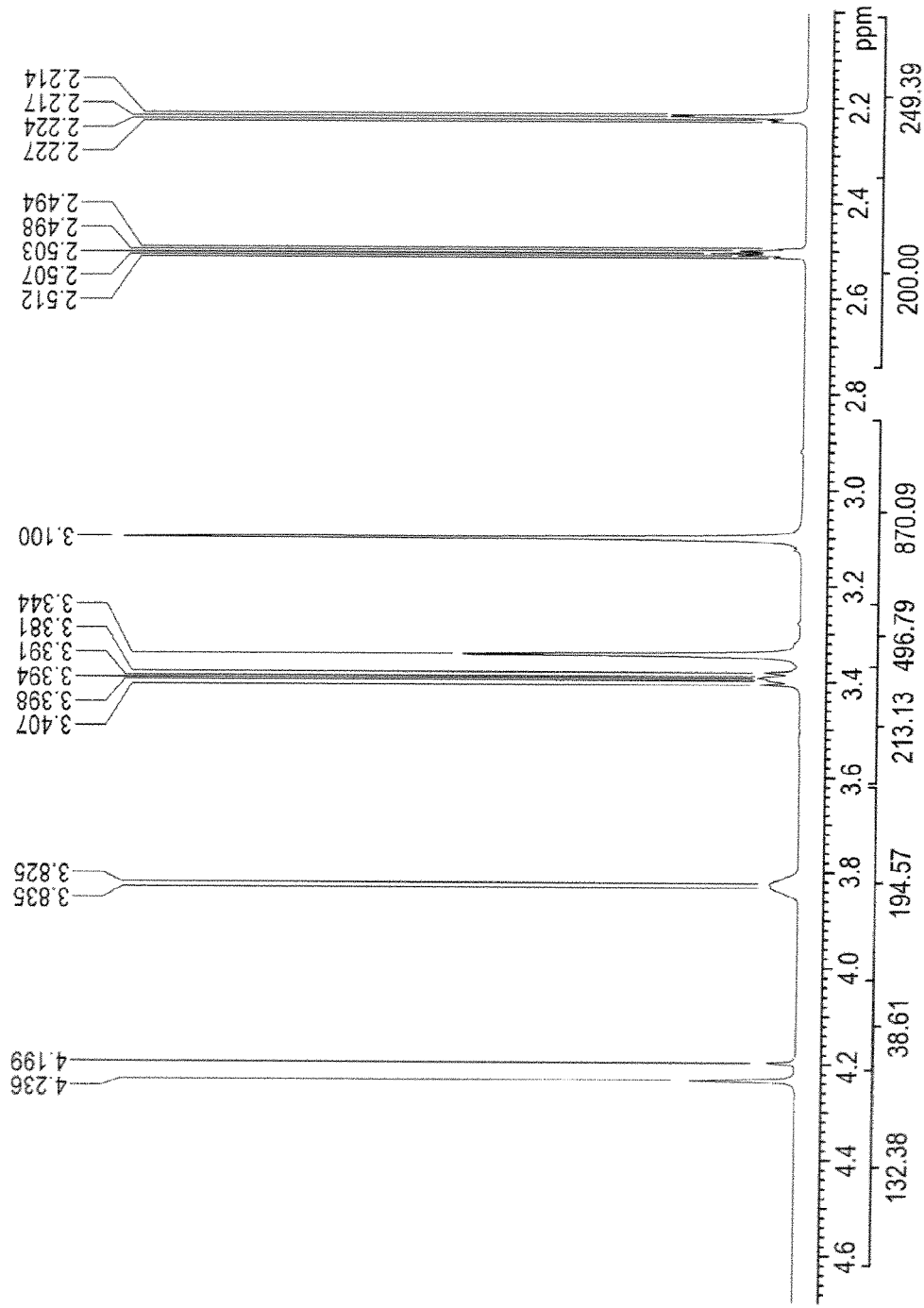
FIG. 5C is an $^1$H-NMR spectrum from 4.6 to 2.2 ppm of an intermediate product useful in an exemplary method of making a choline hydrogen diacid cocrystal of epalrestat according to one embodiment of the invention.

A slurry of 265 mg (0.83 mmol) of epalrestat free acid and 20 mL of absolute ethanol was treated with 0.187 mL of 50% aqueous choline hydroxide (0.187 mL with a density of 1.073 g/mL-201 mg 50% choline hydroxide by weight=101 mg, 0.83 mmol of choline hydroxide). During the addition, all of the solid dissolved. The resulting solution was poured into 400 mL of diethyl ether and the precipitated solids were collected by filtration to give 282 mg of product. The solids were dried in a vacuum oven at 1-5 torr pressure and ambient temperature overnight. The solids were collected and analytical data were obtained on the intermediate product: the XRPD pattern was as shown in FIG. 4, and the $^1$H-NMR spectrum was as shown in FIGS. 5A-5C.

Example 2—Preparation of a Choline Hydrogen Diacid Cocrystal of Epalrestat

A mixture of 209 mg of epalrestat free acid and II mL acetone was sonicated briefly and filtered through a 0.2 micron nylon filter. The filtrate was treated with 39 mg of the intermediate product of Example 1 to give a slurry. The slurry was agitated by placing it in a capped vial on a rotating wheel for about 4 days. Filtration afforded 56 mg of solid choline hydrogen diepalrestat. Analytical data were obtained on the product: the XRPD pattern is shown in FIG. 1, the DSC thermogram is shown in FIG. 2, and the $^1$H-NMR spectrum is shown in FIGS. 3A-3D. Elemental analysis was as follows:

|  | % C | % H | % N | % S |
|---|---|---|---|---|
| Experimental (1B) | 54.13 | 4.48 | 5.40 | 17.11 |
| Theoretical | 56.66 | 5.30 | 5.66 | 17.29 |

Example 3—Preparation of a Choline Hydrogen Diacid Cocrystal of Epalrestat

Figure 6B:
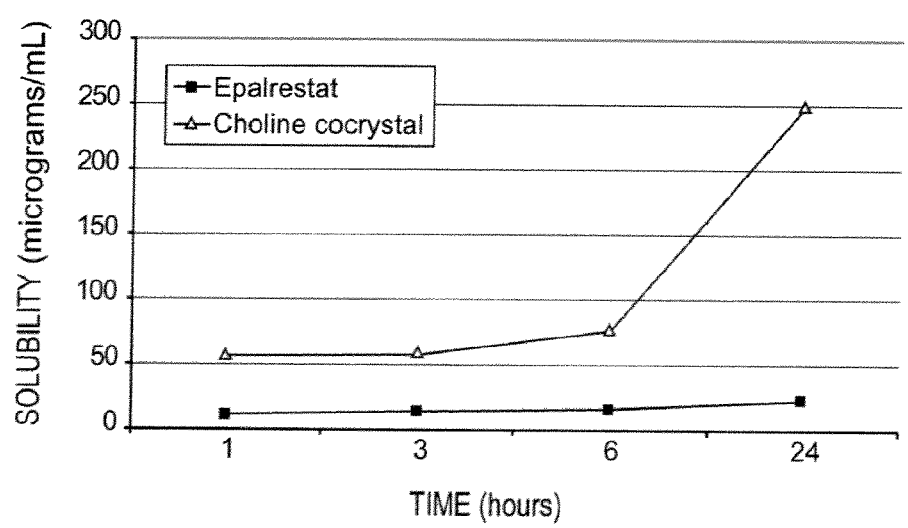

A mixture of 85 mg of epalrestat free acid and 20 mL of absolute ethanol was briefly sonicated and filtered through a 0.2 micron nylon filter. The filtrate was treated with 26 mg of the intermediate product of Example 1 with sonication to give a slurry. The slurry was agitated by placing it in a capped vial on a rotating wheel for about 4 days. Filtration afforded 36 mg of solid choline hydrogen diepalrestat. Analytical data were obtained on the product: the XRPD pattern was substantially as shown in FIG. 1. Solubility data were obtained in water on the final product, and the solubility profile is shown in FIG. 6A. As can be seen in FIG. 6A, the dissolved concentration of epalrestat increased over time to 249 µg/mL after approximately 24 hours. As can be seen in FIG. 6B, the choline hydrogen diacid cocrystal of epalrestat appears to have a greater solubility in water than the free acid.

What is claimed is:

1. A method of treating any of the following conditions comprising administering a pharmaceutical composition comprising a choline hydrogen diacid cocrystal of 5[(1Z,2E)-2-methyl-3-phenylpropenylidene]-4-oxo-2-thioxo-3-thiazolidineacetic acid having an XRPD pattern substantially similar to that in FIG. 1: diabetic nephropathy, diabetic cardiomyopathy, or diabetic retinopathy.

2. A method of delaying the onset of, or lessening the degree to which a patient develops, any of the following conditions comprising administering a pharmaceutical composition comprising a choline hydrogen diacid cocrystal of 5[(1Z,2E)-2-methyl-3-phenylpropenylidene]-4-oxo-2-thioxo-3-thiazolidineacetic acid having an XRPD pattern substantially similar to that in FIG. 1: cardiac tissue ischemia, diabetic neuropathy, diabetic nephropathy, diabetic cardiomyopathy, diabetic retinopathy, diabetic gastroparesis, cataracts, foot ulcers, diabetic macroangiopathy, and diabetic microangiopathy.

3. The method according to claim 1, wherein the pharmaceutical composition comprises an amount of the choline hydrogen diacid cocrystal of 5[(1Z,2E)-2-methyl-3-phenyl-propenylidene]-4-oxo-2-thioxo-3-thiazolidineacetic acid effective to treat said condition.

4. The method according to claim 1, wherein the pharmaceutical composition comprises an amount of the choline hydrogen diacid cocrystal of 5[(1Z,2E)-2-methyl-3-phenyl-propenylidene]-4-oxo-2-thioxo-3-thiazolidineacetic acid less than the amount effective to treat said condition, and
wherein the pharmaceutical composition further comprises at least one additional compound or form of 5[(1Z,2E)-2-methyl-3-phenylpropenylidene]-4-oxo-2-thioxo-3-thiazolidineacetic acid which, when combined with the choline hydrogen diacid cocrystal of 5[(1Z,2E)-2-methyl-3-phenylpropenylidene]-4-oxo-2-thioxo-3-thiazolidineacetic acid, provides a combined effective amount for treating said condition.

5. The method according to claim 1, wherein the pharmaceutical composition further comprises a pharmaceutically acceptable carrier and/or excipient.

6. The method according to claim 1, wherein the pharmaceutical composition is suitable for preserving the cocrystal form of the choline hydrogen diacid cocrystal of 5[(1Z,2E)-2-methyl-3-phenylpropenylidene]-4-oxo-2-thioxo-3-thiazolidineacetic acid.

7. The method according to claim 1, wherein the pharmaceutical composition comprises an amount of the choline hydrogen diacid cocrystal of 5[(1Z,2E)-2-methyl-3-phenyl-propenylidene]-4-oxo-2-thioxo-3-thiazolidineacetic acid to provide a dosage ranging from about 0.001 mg/kg to about 50 mg/kg per day.

8. The method according to claim 1, wherein the pharmaceutical composition is administered once daily.

9. The method according to claim 1, wherein the pharmaceutical composition is administered two or more times per day.

10. The method according to claim 2, wherein the pharmaceutical composition comprises an amount of the choline hydrogen diacid cocrystal of 5[(1Z,2E)-2-methyl-3-phenyl-propenylidene]-4-oxo-2-thioxo-3-thiazolidineacetic acid effective to delay the onset of, or lessen the degree to which a patient develops, said condition.

11. The method according to claim 2, wherein the pharmaceutical composition comprises an amount of the choline hydrogen diacid cocrystal of 5[(1Z,2E)-2-methyl-3-phenyl-propenylidene]-4-oxo-2-thioxo-3-thiazolidineacetic acid less than the amount effective to delay the onset of, or lessen the degree to which a patient develops, said condition, and
wherein the pharmaceutical composition further comprises at least one additional compound or form of 5[(1Z,2E)-2-methyl-3-phenylpropenylidene]-4-oxo-2-thioxo-3-thiazolidineacetic acid which, when combined with the choline hydrogen diacid cocrystal of 5[(1Z,2E)-2-methyl-3-phenylpropenylidene]-4-oxo-2-thioxo-3-thiazolidineacetic acid, provides a combined effective amount for delaying the onset of, or lessening the degree to which a patient develops, said condition.

12. The method according to claim 2, wherein the pharmaceutical composition further comprises a pharmaceutically acceptable carrier and/or excipient.

13. The method according to claim 2, wherein the pharmaceutical composition is suitable for preserving the cocrystal form of the choline hydrogen diacid cocrystal of 5[(1Z,2E)-2-methyl-3-phenylpropenylidene]-4-oxo-2-thioxo-3-thiazolidineacetic acid.

14. The method according to claim 2, wherein the pharmaceutical composition comprises an amount of the choline hydrogen diacid cocrystal of 5[(1Z,2E)-2-methyl-3-phenyl-propenylidene]-4-oxo-2-thioxo-3-thiazolidineacetic acid to provide a dosage ranging from about 0.001 mg/kg to about 50 mg/kg per day.

15. The method according to claim 2, wherein the pharmaceutical composition is administered once daily.

16. The method according to claim 2, wherein the pharmaceutical composition is administered two or more times per day.

* * * * *